United States Patent
Park et al.

(10) Patent No.: US 11,284,843 B2
(45) Date of Patent: Mar. 29, 2022

(54) APPARATUS AND METHOD FOR ESTIMATING BIO-INFORMATION

(71) Applicant: SAMSUNG ELECTRONICS CO., LTD., Suwon-si (KR)

(72) Inventors: Chang Soon Park, Chungju-si (KR); Ui Kun Kwon, Hwaseong-si (KR); Yunseo Ku, Gwacheon-si (KR); Seung Woo Noh, Seongnam-si (KR); Seung Keun Yoon, Seoul (KR); Dae Geun Jang, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 218 days.

(21) Appl. No.: 16/273,293

(22) Filed: Feb. 12, 2019

(65) Prior Publication Data
US 2019/0254610 A1    Aug. 22, 2019

(30) Foreign Application Priority Data

Feb. 19, 2018 (KR) .................. 10-2018-0019441
Jan. 8, 2019 (KR) .................. 10-2019-0002484

(51) Int. Cl.
*A61B 5/021* (2006.01)
*G16H 50/30* (2018.01)
(Continued)

(52) U.S. Cl.
CPC ............ *A61B 5/7225* (2013.01); *A61B 5/021* (2013.01); *A61B 5/14532* (2013.01);
(Continued)

(58) Field of Classification Search
CPC ... A61B 5/7225; A61B 5/021; A61B 5/14532; A61B 5/14546; G16H 50/30; G16H 50/20
See application file for complete search history.

(56) References Cited

U.S. PATENT DOCUMENTS

| | | | |
|---|---|---|---|
| 7,035,679 B2 | | 4/2006 | Addison et al. |
| 8,463,347 B2 | | 6/2013 | Watson et al. |
| 2005/0070774 A1 | | 3/2005 | Addison et al. |

(Continued)

FOREIGN PATENT DOCUMENTS

| | | |
|---|---|---|
| JP | 2000-218 A | 1/2000 |
| JP | 2008-212745 A | 9/2008 |

(Continued)

OTHER PUBLICATIONS

Criée, C. P., Sorichter, S., Smith, H. J., Kardos, P., Merget, R., Heise, D., . . . & Mitfessel, H. (2011). Body plethysmography—its principles and clinical use. Respiratory medicine, 105(7), 959-971. (Year: 2011).*

(Continued)

*Primary Examiner* — Patrick Fernandes
*Assistant Examiner* — Liam A Wallace
(74) *Attorney, Agent, or Firm* — Sughrue Mion, PLLC

(57) ABSTRACT

An apparatus for estimating bio-information may include: a bio-signal acquirer configured to acquire a bio-signal; and a processor configured to extract one or more first feature values from the bio-signal, determine a scale factor based on the first feature values, and to estimate bio-information based on the scale factor and the first feature values.

15 Claims, 9 Drawing Sheets

(51) Int. Cl.
  *G16H 50/20* (2018.01)
  *A61B 5/00* (2006.01)
  *A61B 5/145* (2006.01)

(52) U.S. Cl.
  CPC ......... *A61B 5/14546* (2013.01); *G16H 50/20* (2018.01); *G16H 50/30* (2018.01)

(56) References Cited

U.S. PATENT DOCUMENTS

| | | |
|---|---|---|
| 2005/0080462 A1 | 4/2005 | Jenkins et al. |
| 2011/0034813 A1 | 2/2011 | Cohen et al. |
| 2014/0066732 A1* | 3/2014 | Addison ................ A61B 5/029 600/324 |
| 2015/0313486 A1 | 11/2015 | Mestha et al. |

FOREIGN PATENT DOCUMENTS

| | | | | |
|---|---|---|---|---|
| KR | 10-0638696 B1 | 10/2006 | | |
| KR | 10-0660349 B1 | 12/2006 | | |
| KR | 10-0820159 B1 | 4/2008 | | |
| KR | 10-1352479 B1 | 1/2014 | | |
| KR | 10-1503604 B1 | 3/2015 | | |
| KR | 10-1689401 B1 | 12/2016 | | |
| WO | WO-2014081958 A1 * | 5/2014 | ........... | A61B 5/7275 |
| WO | WO-2017066149 A1 * | 4/2017 | ......... | A61B 5/02125 |

OTHER PUBLICATIONS

Search Report dated Jul. 15, 2019 by the European Patent Office in counterpart European Patent Application No. 19157663.6.

* cited by examiner

APPARATUS AND METHOD FOR ESTIMATING BIO-INFORMATION

CROSS-REFERENCE TO RELATED APPLICATION(S)

This application claims priority from Korean Patent Application No. 10-2018-0019441, filed on Feb. 19, 2018, in the Korean Intellectual Property Office and Korean Patent Application No. 10-2019-0002484, filed on Jan. 8, 2019, in the Korean Intellectual Property Office, the disclosures of which are incorporated herein by reference in their entireties.

BACKGROUND

1. Field

Apparatuses and methods consistent with example embodiments relate to non-invasively estimating bio-information using bio-signals.

2. Description of the Related Art

Recently, with the aging population, soaring medical costs, and a shortage of medical personnel for specialized medical services, research is being actively conducted on tech convergence for medical devices.

Particularly, monitoring of the health condition of the human body is not limited to medical institutions, but is expanding to mobile healthcare fields that may monitor a user's health condition anywhere and anytime in daily life at home or office.

Typical examples of bio-signals, which indicate the health condition of individuals, include an electrocardiography (ECG) signal, a photoplethysmogram (PPG) signal, an electromyography (EMG) signal, and the like, and various bio-signal sensors have been developed to measure these signals in daily life.

For example, according to studies on the PPG signal, the entire PPG signal is a superposition of propagation waves starting from the heart toward the distal end portions of the body and reflection waves returning back from the distal end portions.

Further, it has been known that information for estimating blood pressure may be obtained by extracting various features associated with the propagation waves or the reflection waves.

In some cases, however, the method of estimating bio-information from bio-signals to monitor health conditions in daily life may provide an unstable estimation result of bio-information due to deterioration in bio-signal quality, interference of motion noise, and the like, and various studies have been conducted to solve the problem.

SUMMARY

Example embodiments address at least the above problems and/or disadvantages and other disadvantages not described above. Also, the example embodiments are not required to overcome the disadvantages described above, and may not overcome any of the problems described above.

One or more example embodiments provide an apparatus and a method for estimating bio-information, in which scale conversion is performed on features extracted from a bio-signal, and therefore bio-information may be estimated accurately and stably even when the bio-signal is measured in an unstable environment.

According to an aspect of an example embodiment, there is provided an apparatus for estimating bio-information, the apparatus including: a bio-signal acquirer configured to acquire a bio-signal; and a processor configured to extract one or more first feature values from the bio-signal, determine a scale factor based on the first feature values, and estimate bio-information based on the scale factor and the first feature values.

The first features may include a feature associated with cardiac output (CO), a feature associated with total peripheral resistance (TPR), and a combination of the feature associated with CO and the feature associated with the TPR.

The processor may calculate a second feature value by combining the first feature values, may calculate based on the second feature value, and may adjust a reference scale factor based on the scale control ratio to determine the scale factor.

Further, the processor may calculate the second feature value by combining at least one of an individual variation and a combined variation of the first feature values.

The processor may calculate the scale control ratio according to a magnitude of the second feature value by applying the second feature value to a scale control ratio decision function.

Here, the scale control ratio decision function may be expressed as a graph having a valley shape, in which the scale control ratio has a minimum value at a point of a reference second feature value and increases with a change in the second feature value from the reference second feature value, and the scale control ratio is saturated to a predetermined scale control ratio in an area of the graph where the second feature value falls outside a threshold range.

The processor may calculate individual scale control ratios for the first feature values, may calculate a scale control ratio based on a statistical value of the individual scale control ratios, and may determine the scale factor based on the scale control ratio.

In addition, the processor may calculate a third feature value by combining the first feature values, and may estimate bio-information based on the third feature value and the scale factor.

Moreover, the processor may estimate the bio-information by multiplying a difference between the third feature value and a reference third feature value by the scale factor, and adding an offset value to the multiplied difference.

In response to the first feature value exceeding a predetermined threshold value, the processor may determine a reference scale factor to be the scale factor.

The processor may normalize the first feature values based on a reference first feature value.

The apparatus for estimating bio-information may further including an output interface configured to output the bio-signal, feature values of the bio-signal, a multiplication coefficient ratio control factor, a multiplication coefficient ratio, and the bio-information.

The bio-information may include blood pressure, pulse, cardiac output, blood glucose, triglycerides, and keratin.

According to an aspect of another example embodiment, there is provided a method of estimating bio-information, the method including: acquiring a bio-signal; extracting one or more first feature values from the bio-signal; determining a scale factor based on the first feature values; and estimating bio-information based on the scale factor and the first feature values.

The determining of the scale factor may include: calculating a second feature value by combining the first feature values; calculating a scale control ratio based on the second feature value; and determining the scale factor by adjusting a reference scale factor based on the scale control ratio.

Further, the calculating of the second feature value may include combining at least one of an individual variation and a combined variation of the first feature values.

In this case, the calculating of the scale control ratio may include calculating the scale control ratio according to a magnitude of the second feature value by applying the calculated second feature value to a scale control ratio decision function.

In addition, the scale control ratio decision function may be expressed as a graph having a valley shape, in which the scale control ratio has a minimum value at a point of a reference second feature value and increases with a change in the second feature value from the reference second feature value, and the scale control ratio is saturated to a predetermined scale control ratio in an area of the graph where the second feature value falls outside a threshold range.

In this case, the determining of the scale factor may include: calculating individual scale control ratios for the first feature values; calculating a scale control ratio based on a statistical value of the individual scale control ratios; and determining the scale factor by adjusting the reference scale factor based on the calculated scale control ratio.

In addition, the estimating of the bio-information may include: calculating a third feature value by combining the first feature values; and multiplying a difference between the third feature value and a reference third feature value by the scale factor, and adding an offset value to the multiplied difference to estimate the bio-information.

The determining of the scale factor may include: determining whether the first feature value exceeds a predetermined threshold value; and upon determining that the first feature value exceeds the predetermined threshold value, determining a reference scale factor to be the scale factor.

BRIEF DESCRIPTION OF THE DRAWINGS

The above and/or other aspects will be more apparent by describing certain example embodiments, with reference to the accompanying drawings, in which.

DETAILED DESCRIPTION

Figure 1:
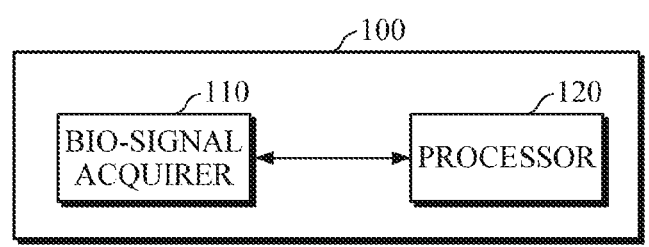
FIG. 1 is a block diagram illustrating an apparatus for estimating bio-information according to an example embodiment.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

Process steps described herein may be performed differently from a specified order, unless a specified order is clearly stated in the context of the disclosure. That is, each step may be performed in a specified order, at substantially the same time, or in a reverse order.

Further, the terms used throughout this specification are defined in consideration of the functions according to example embodiments, and can be varied according to a purpose of a user or manager, or precedent and so on. Therefore, definitions of the terms should be made on the basis of the overall context.

It will be understood that, although the terms first, second, etc. may be used herein to describe various elements, these elements should not be limited by these terms. These terms are only used to distinguish one element from another. Any references to singular may include plural unless expressly stated otherwise. In the present specification, it should be understood that the terms, such as 'including' or 'having.' etc., are intended to indicate the existence of the features, numbers, steps, actions, components, parts. or combinations thereof disclosed in the specification, and are not intended to preclude the possibility that one or more other features, numbers, steps, actions, components, parts, or combinations thereof may exist or may be added.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Figure 2:
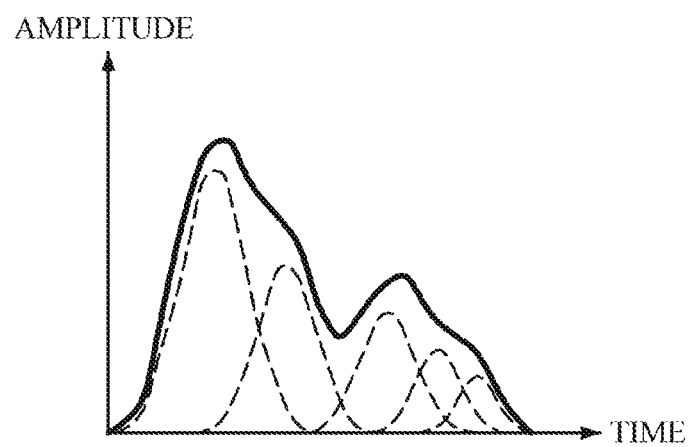
FIG. 2 is a diagram illustrating a bio-signal according to an example embodiment.

FIG. 1 is a block diagram illustrating an apparatus for estimating bio-information according to an example embodiment, and FIG. 2 is a diagram illustrating a bio-signal according to an example embodiment.

The bio-information estimating apparatus 100 may acquire a bio-signal, may extract features from the acquired bio-signal, and may estimate bio-information based on the extracted features.

For example, the bio-information estimating apparatus 100 may extract a first feature from a photoplethysmography (PPG) signal which is composed of a superposition of propagation waves and reflection waves illustrated in FIG. 2, and may estimate blood pressure by multiplying the first feature by a scale factor, and by adding an offset value, such as a blood pressure value in a stable state, to the multiplied first feature. Here, the first feature may include a feature $f_{1\_co}$ associated with cardiac output (CO), a feature $f_{1\_TPR}$ associated with total peripheral resistance (TPR), a combination thereof, and the like, in which the combination may include addition, subtraction, multiplication, division, and the like of the feature $f_{1\_co}$ associated with cardiac output (CO) and the feature $f_{1\_TPR}$ associated with total peripheral resistance (TPR), and may include further adding or subtracting a real number to and from the added, subtracted, multiplied, divided value, and the like. Cardiac output (CO) is the amount of blood the heart pumps out over a unit of time. The total peripheral resistance (TPR) is a total resistance offered by systemic arteries to the blood flow across the systemic arteries. For example, the feature $f_{1\_co}$ associated with cardiac output (CO) and the feature $f_{1\_TPR}$ associated with total peripheral resistance (TPR) may be obtained by extracting at least one feature point in a PPG signal (e.g., a peak point of the PPG signal, a peak point of each of the propagation wave and the reflection waves), extracting time and/or an amplitude of the at least one feature point and linearly or non-linearly combining the time and/or the amplitude of the at least one feature point, but the example embodiment is not limited therefore. Doppler ultrasound, thoracic bioimpedance, pulse contour analysis, or multi-linear regression analysis based on a pulse width of a PPG signal may be used to extract the feature $f_{1\_co}$ associated with cardiac output (CO) and feature $f_{1\_TPR}$ associated with total peripheral resistance (TPR).

In this case, the bio-information estimating apparatus 100 may stably estimate bio-information by calculating an adaptive scale factor based on a variation of the extracted first features.

The bio-information estimation apparatus 100 may calculate a scale control ratio for adjusting a scale factor based on the extracted first feature, and may determine a scale factor adaptively to the variation of the first feature values by adjusting a reference scale factor based on the calculated scale control ratio. For example, the reference scale factor may have a predetermined value, and the scale control ratio may have a value that is higher than 0 and less than or equal to 1. If the extracted first feature has a value greater than a predetermined threshold, the scale control ratio may have a value of 1 so that the bio-information is estimated using the reference scale factor without adjustment of the reference scale factor. If the extracted first feature has a value less than or equal to the predetermined threshold, the scale control ratio may have a value between 0 and 1 and the reference scale factor may be scaled down according to the value of the scale control ratio.

As described above, by adaptively determining the scale factor, the bio-information estimating apparatus 100 may stably estimate bio-information even when a bio-signal is estimated in a poor environment, such as in the case where an unstable bio-signal is acquired due to motion noise and the like.

Figure 3:
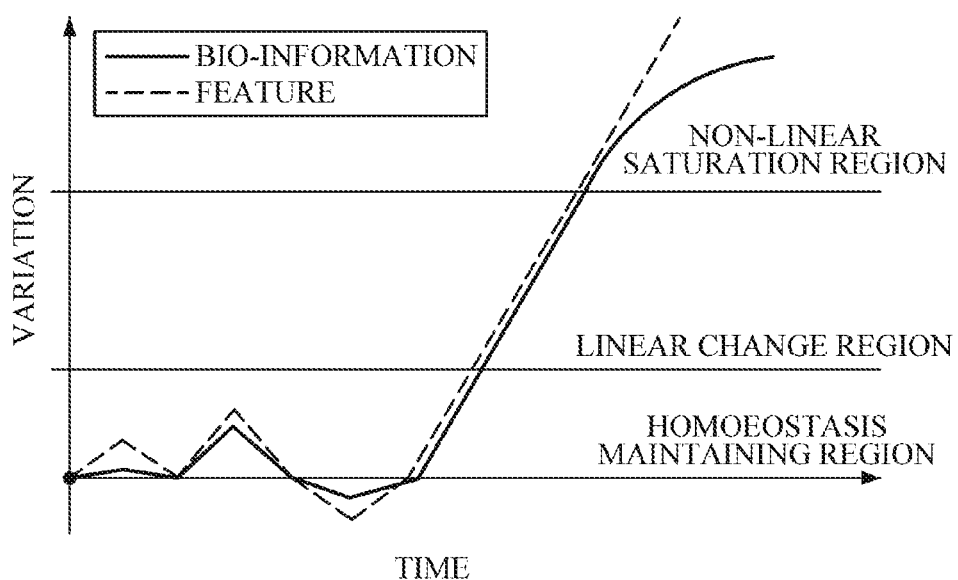
FIG. 3 is a diagram explaining an example of adjusting a scale factor according to an example embodiment.

FIG. 3 is a diagram explaining an example of adjusting a scale factor according to an example embodiment.

Referring to FIG. 3, depending on whether a variation of features (e.g., features $f_{1\_co}$ and $f_{1\_TPR}$) extracted from a bio-signal belongs to a homoeostasis maintaining region, a linear change region, or a non-linear saturation region, a changing shape of bio-information may vary with respect to a change in the features extracted from the bio-signal.

For example, in the homoeostasis maintaining region, a variation of bio-information is smaller than a change in features of the bio-signal according to human body characteristics of maintaining homoeostasis; in the linear change region, the variation of bio-information has a predetermined correlation with the change in features of the bio-signal; and in the non-linear saturation region, bio-information changes irregularly having a non-linear correlation or no specific correlation with the change in features of the bio-signal.

Accordingly, the bio-information estimating apparatus 100 may determine whether the first feature value extracted from the bio-signal or a variation in the first feature value belongs to the homoeostasis maintaining region, the linear change region, or the non-linear saturation region, and may estimate bio-information stably and accurately by adjusting a scale factor based on the determination.

More specifically, the bio-information estimating apparatus 100 may determine that the first feature value belongs to the homoeostasis maintaining region when the variation in the first feature value is greater than the variation in the bio-signal, may determine that the first feature value belongs to the linear change region when the correlation between the variation in the first feature and the variation in the bio-signal is greater than equal to a predetermined correlation value, and may determine that the first feature value belongs to the non-linear saturation region when the correlation between the variation in the first feature and the variation in the bio-signal is less than the predetermined correlation value.

For example, in the case where the first feature value belongs to the homoeostasis maintaining region, the bio-information estimating apparatus 100 may decrease a scale factor by considering homoeostasis maintaining characteristics, and thus may reduce an effect of the change in the first feature value on the change in bio-information.

In another example, in the case where the first feature value belongs to the linear change region, the bio-information estimating apparatus 100 may determine a predetermined reference scale factor to be a scale factor, such that the change in the first feature value may be reflected as it is in the bio-information.

In yet another example, in the case where the first feature value belongs to the non-linear saturation region, the bio-information estimating apparatus 100 may adjust a scale factor by applying the first feature value to a bio-information estimation model, which is pre-generated by a non-linear function or machine learning, so that the change in the first feature value may be reflected in the change of bio-information.

As described above, by adjusting a scale factor according to the change in the features extracted from the bio-signal, the bio-information estimating apparatus 100 may accept a feature change as it is, which may affect estimation of bio-information, and may reflect the feature change in estimation of bio-information. Further, the bio-information estimating apparatus 100 may adaptively decrease a feature change, which does not affect estimation of bio-information, and may reduce error caused by unnecessary motion noise. Accordingly, the bio-information estimating apparatus 100 may stably estimate bio-information even in an environment where an unstable bio-signal is measured.

For convenience of explanation, the following description will be made using an example of estimating blood pressure based on a bio-signal. However, bio-information is not limited thereto, and may include blood pressure, pulse, oxygen saturation, stress index, blood glucose, triglycerides, keratin, and the like.

Referring back to FIG. 1, an example of estimating bio-information by the bio-information estimating apparatus 100 will be described in detail below.

As illustrated in FIG. 1, the bio-information estimating apparatus 100 includes a bio-signal acquirer 110 and a processor 120. Here, the processor 120 may be composed of one or more processors, a memory, and a combination thereof.

The bio-signal acquirer 110 may acquire a bio-signal of a user.

Here, the bio-signal may include an electrocardiogram (ECG) signal, a photoplethysmography (PPG) signal, an electromyography (EMG) signal, a ballistocardiogram (BCG) signal, a cardiac output (CO) signal, a Total peripheral resistance (TPR) signal, heart sound, and the like.

For example, the bio-signal acquirer 110 may include a sensor including at least one of the following: one or more electrodes for measuring a bio-signal, a PPG sensor, an ECG sensor, a pressure sensor, and a photodetector module including a light source and a detector. The bio-signal acquirer 110 may directly interface with a user through the sensor to acquire a bio-signal.

Further, the bio-signal acquirer 110 may include a communication interface to communicate with an external device to receive bio-signal data of a user from the external device. For example, the bio-signal acquirer 110 may receive bio-signal data of a user from the external device using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, and the like. In addition, examples of the external device may include a cellular phone, a smartphone, a tablet PC, a laptop computer, a personal digital assistant (PDA), a portable multimedia player (PMP), a navigation, an MP3 player, a digital camera, a wearable device, and the like. However, the external device is not limited to the above examples, and may include various devices which store bio-signal data of a user.

The processor 120 may extract one or more first feature values $f_1$ from the acquired bio-signal.

The first feature values, which are extracted from the bio-signal, may indicate features having a predetermined correlation with bio-information desired to be estimated. One or more first feature values may be extracted; and in the case of estimating blood pressure by using, for example, the bio-information estimating apparatus 100, the first features may include a feature $f_{1\_co}$ associated with cardiac output (CO) which indicates the blood volume pumped by the heart in one minute, a feature $f_{1\_TPR}$ associated with total peripheral resistance (TPR), a combination thereof, and the like. The first features may vary depending on the types of bio-information desired to be estimated.

Upon extracting the first feature values from the bio-signal, the processor 120 may convert the first feature values.

For example, the processor 120 may normalize the extracted first feature values by dividing the first feature value (e.g., $f_{1\_co\_norm} = f_{1\_co}/f_{1\_co\_ref}$, $f_{1\_TPR\_norm} = f_{1\_TPR}/f_{1\_TPR\_ref}$, etc.), extracted from the bio-signal, by a reference first feature value extracted in a reference state (e.g., $f_{1\_co\_ref}$, $f_{1\_TPR\_ref}$ etc.).

In this case, the reference state is a resting state except for a sleep state, and may refer to, for example, a state in which pulse and respiration rates are stable or a state in which blood pressure measured by an external device for measuring blood pressure is maintained without substantial change. The reference state may be measured from a test subject while the test subject is awake and resting without exercising.

Further, a reference second feature value and a reference third value, which will be described later, may refer to a second feature value and a third feature value which are calculated based on the reference first feature value extracted in the reference state. Hereinafter, the first feature value may refer to the first feature value normalized using the reference first feature value.

The processor 120 may determine a scale factor based on the extracted first feature values.

The scale factor may be a coefficient for adjusting a scale of the first feature value extracted for estimating bio-information, but is not limited thereto, and may be a coefficient for adjusting a scale of the third feature value calculated based on the first feature value for estimating bio-information, as will be described later.

For example, the processor 120 may calculate a second feature value $f_{sc}$ by combining the first feature values, and may calculate a scale control ratio based on the second feature value.

Here, the second feature value may indicate a feature value for determining the scale control ratio, and the processor 120 may calculate the second feature value using an individual variation or a combined variation of first feature values.

Figure 4:
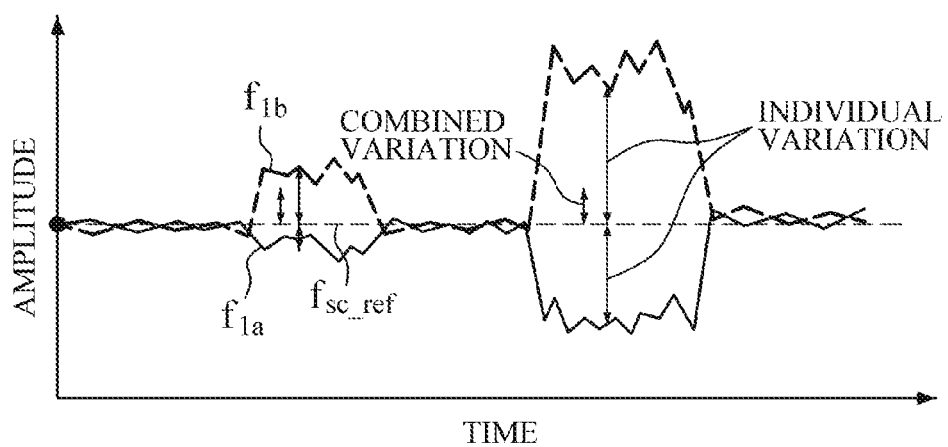
FIG. 4 is a diagram explaining an example of calculating a second feature value according to an example embodiment.

FIG. 4 is a diagram explaining an example of calculating a second feature value according to an example embodiment.

Referring to FIGS. 1 and 4, FIG. 4 illustrates a variation in first feature values $f_{1a}$ and $f_{1b}$ according to elapsed time. In particular, the processor 120 may calculate the variation in the first feature values based on a reference second feature value $f_{sc,ref}$.

Upon calculating one or more first feature values, the processor 120 may calculate a second feature value by using an individual variation and/or a combined variation of the first feature values.

In this case, the combined variation may refer to a difference between a value, obtained by linear combination of the first feature values $f_{1a}$ and $f_{1b}$ (e.g., addition, subtraction, and multiplication of $f_{1a}$ and $f_{1b}$, a combination thereof, etc.), and the reference second feature value $f_{sc,ref}$; and the individual variation may refer to a difference between each of the first feature values $f_{1a}$ and $f_{1b}$ and the reference second feature value $f_{sc,ref}$.

For example, the following Equation 1 may represent an example of calculating the second feature value $f_{sc}$ by using the combined variation of the first feature values $f_{1a}$ and $f_{1b}$.

$$f_{sc} = f_{1a} + f_{1b} - f_{sc,ref} \quad \text{[Equation 1]}$$

Further, the following Equation 2 may represent another example of calculating the second feature value $f_{sc}$ by using the individual variation of the first feature values $f_{1a}$ and $f_{1b}$.

$$f_{sc} = (f_{1a} - f_{1b} + |f_{1a} - f_{sc,ref}| + |f_{1b} - f_{sc,ref}|)/2 \quad \text{[Equation 2]}$$

In addition, the following Equation 3 may represent yet another example of calculating the second feature $f_{sc}$ by using a combination of the combined variation and the individual variation of the first feature values $f_{1a}$ and $f_{1b}$.

$$f_{sc} = (f_{1a} + f_{1b} + |f_{1a} - f_{sc,ref}| + |f_{1b} - f_{sc,ref}|)/2 \quad \text{[Equation 3]}$$

As described above, the processor 120 may calculate the second feature value $f_{sc}$ for determining a scale control ratio by using individual first feature values $f_{1a}$ and $f_{1b}$ and/or a combination thereof.

In another example, the processor 120 may calculate the second feature value $f_{sc}$ by applying a weight to a first feature value, having a higher correlation with bio-information to be estimated than other first feature values among the extracted first feature values, which is represented by the following Equation 4.

$$f_{sc}=\alpha*f_{1a}+\beta*f_{1b}-f_{sc\_ref}$$ [Equation 4]

$\alpha$ and $\beta$ may denote weights that are respectively applied to the first feature values $f_{1a}$ and $f_{1b}$. $\alpha$ may have a value greater than $\beta$ when the correlation between the first feature value $f_{1a}$ and the bio-information is greater than the correlation between the first feature value $f_{1b}$ and the bio-information.

Equations 1 to 4 may represent examples of calculating the second feature value, but the calculation of the second feature value is not limited thereto, and the second feature value for determining a scale control ratio may be determined by various combinations of the first feature values.

Upon calculating the second feature value, the processor 120 may calculate the scale control ratio based on the second feature value, and may determine a scale factor by adjusting a reference scale factor based on the calculated scale control ratio.

Based on a magnitude of the calculated second feature value, the processor 120 may determine whether a variation in the first feature value belongs to the homoeostasis maintaining region, the linear change region, or the non-linear saturation region, and may calculate a scale control ratio based on the determination.

For example, in the case where the calculated second feature value belongs to the homoeostasis maintaining region, the processor 120 may decrease a reference scale factor by calculating the scale control ratio to be 1 or lower, and may determine the decreased reference scale factor to be a scale factor, thereby reducing an effect of the change in the first feature value on the change in bio-information.

In another example, in the case where the calculated second feature value belongs to the linear change region, the processor 120 may determine a predetermined reference scale factor to be a scale factor by determining a scale control ratio to be 1. In this manner, by using the predetermined reference scale factor as a scale factor, the processor 120 may reflect the change in the first feature value in the change of bio-information according to the predetermined ratio.

In yet another example, in the case where the second feature value belongs to the non-linear saturation region, the processor 120 may determine a scale control ratio for adjusting the reference scale factor by applying the second feature value to a predetermined scale control estimation model, which is pre-generated by a non-linear function or machine learning, so that the change in the first feature value may be reflected in the change of bio-information.

As described above, the processor 120 may adjust the reference scale factor based on the calculated scale control ratio, and may estimate bio-information by adaptively adjusting the scale factor for estimating bio-information.

The processor 120 may calculate the scale control ratio according to a magnitude of the second feature value by applying the second feature value to a scale control ratio decision function $\rho_{sc}$.

Figure 5:
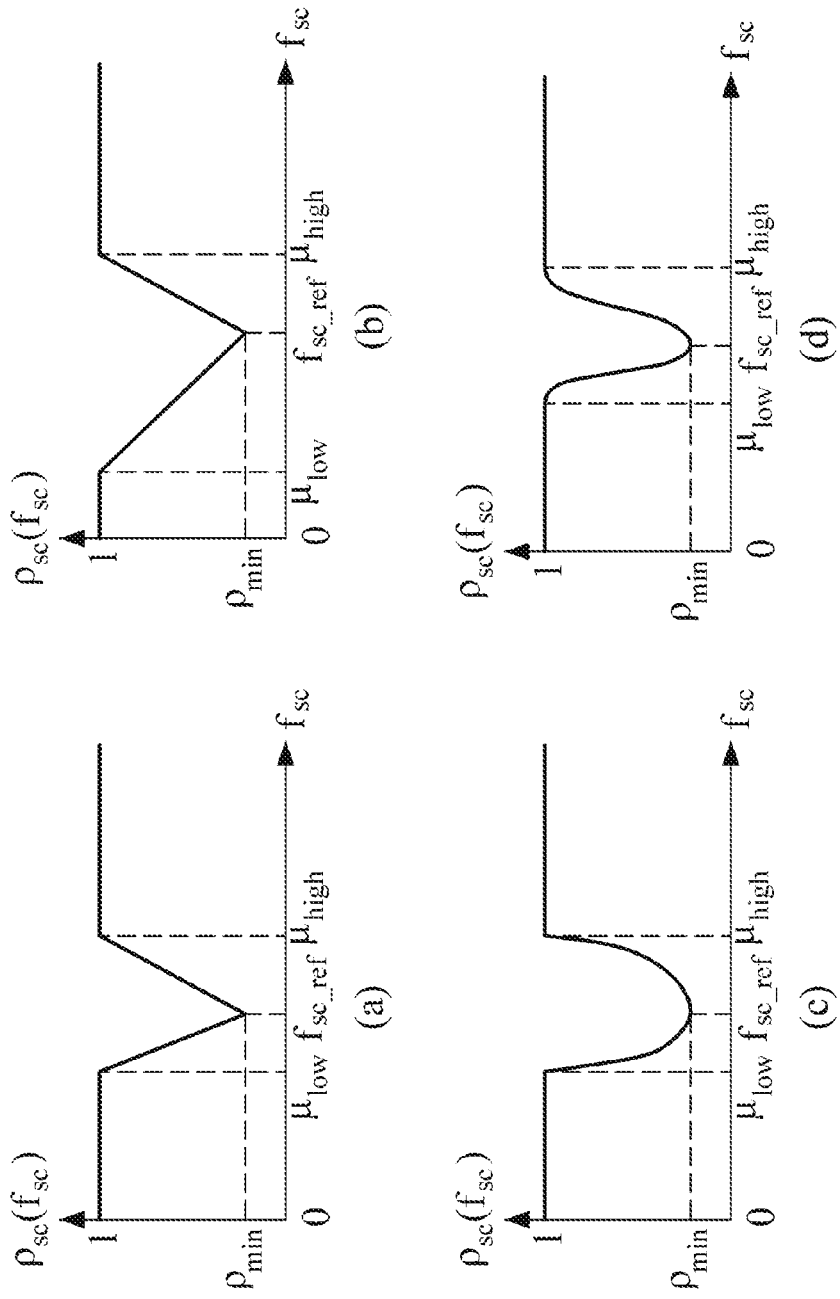
FIG. 5 is a diagram illustrating an example of calculating a scale control ratio according to an example embodiment.

FIG. 5 is a diagram illustrating an example of calculating a scale control ratio according to an example embodiment.

Referring to FIG. 5, a scale control ratio decision function $\rho_{sc}(f_{sc})$ may have a valley shape, in which the scale control ratio has a minimum value $\rho_{min}$ at a point of the reference second feature value $f_{sc\_ref}$, and increases with the change in the second feature value from the reference second feature value, and in the case where the second feature value falls outside a threshold range, the scale control ratio is saturated to a predetermined scale control ratio.

Here, the threshold range may indicate an interval between a low point $\mu_{low}$ and a high point $\mu_{high}$ of the second feature value. In other words, the threshold range may indicate a region where the first feature value is changed from the homoeostasis maintaining region, and a region where the scale control ratio changes adaptively. That is, in the case where the second feature value $f_{sc}$ changes within the predetermined threshold range, the scale control ratio increases in both directions from the reference second feature value.

As described above, since the scale control ratio has a minimum value $\mu_{min}$ at a point of the reference second feature value $f_{sc\_ref}$, the change of bio-signal features in a stable state, such as a reference state, may have a small effect on estimation of bio-information; and as the second feature value deviates from the reference state, the scale control ratio for estimating bio-information increases. Accordingly, as an amplitude of a bio-signal increases, the change of the bio-signal features may have a greater effect on estimation of bio-information.

Then, as the second feature value $f_{sc}$ continuously changes to fall outside the threshold range, the scale control ratio $\rho_{sc}(f_{sc})$ is saturated to a predetermined scale control ratio (e.g., 1), such that the processor 120 may determine the predetermined reference scale factor itself to be a scale factor.

Referring back to FIG. 5, the scale control ratio decision functions (a) and (b) may change linearly from the reference second feature value within a threshold range. However, as can be seen from the scale control ratio decision function (b), a slope of the scale control ratio decision function (a) may be determined differently according to a low point $\mu_{low}$ and a high point $\rho_{high}$ of the second feature value.

In addition, the scale control ratio decision function (c) may be given in the form of a power function of degree n (e.g., quadratic function, etc.) within a threshold range; and the scale control ratio decision function (d) may be given in the form of a trigonometric function (e.g., cosine function, etc.) within a threshold range.

The shape of the graph within a threshold range of the scale control ratio decision function may vary depending on a bio-signal and bio-information to be estimated, and may be pre-generated based on an estimation model, which is pre-generated by machine learning or based on a correlation between the bio-signal and bio-information. Further, the shape of the graph is not limited thereto, and the processor 120 may periodically acquire bio-signals of a user, and may directly generate a scale control ratio decision function from a learning model for generating the scale control ratio decision function.

Further, the processor 120 may calculate individual scale control ratios for the first feature values, and may calculate a scale control ratio based on a statistical value of the individual scale control ratios.

Figure 6:
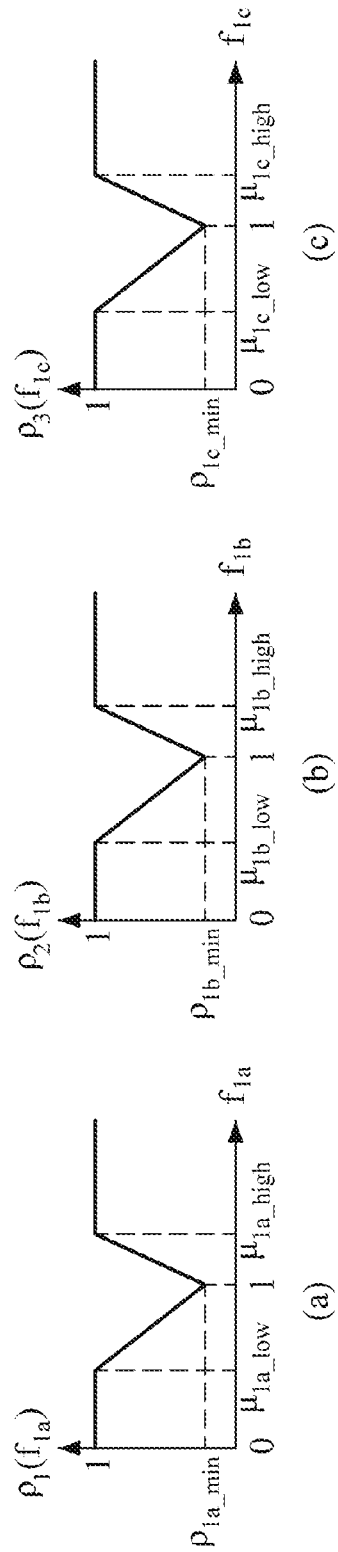
FIG. 6 is a diagram explaining another example of calculating a scale control ratio according to an example embodiment.

FIG. 6 is a diagram explaining an example of calculating a scale control ratio according to another example embodiment.

Referring to FIGS. 1 and 6, the processor 120 may calculate an individual scale control ratio for each of the first feature values based on the scale control ratio decision function for each of the first feature values.

For example, upon extracting first feature values $f_{1a}$, $f_{1b}$, and $f_{1c}$, instead of generating a second feature value by combining the first feature values, the processor 120 may calculate individual scale control ratios $\rho_1$, $\rho_2$, and $\rho_3$ using scale control ratio functions $\rho_1(f_{1a})$, $\rho_2(f_{1b})$, and $\rho_3(f_{1c})$ for each of the first feature values, and may use a statistical value of the individual scale control ratios as a scale control ratio.

For example, the processor 120 may calculate a mean value of the individual scale control ratios (e.g., $\rho=(\rho_1+\rho_2+\rho_3)/3$) as a scale control ratio; and the processor 120 may apply a weighted value to features, having a higher correlation with bio-information to be estimated than other feature values among the extracted first feature values, and may calculate a mean value of the features (e.g., $p=(\alpha^*\rho_1+\beta^*\rho_2+\gamma^*\rho_3)/3$) as a scale control ratio. However, the scale control ratio is not limited thereto, and the processor 120 may calculate a statistical value, such as a maximum value, a minimum value, and a median value, of the individual scale control ratios, as the scale control ratio.

In addition, in response to the first feature value exceeding a predetermined threshold value, the processor 120 may determine the reference scale factor to be a scale factor.

For example, the processor 120 may determine whether the first feature value exceeds a predetermined threshold value.

In one embodiment, the processor 120 may compare the extracted first feature value with a value at a predetermined low point $\mu_{low}$ or a predetermined high point $\mu_{high}$ of the scale control ratio decision function, and may determine whether the first feature value is lower than the predetermined low point $\mu_{low}$ or higher than the predetermined high point $\mu_{high}$.

That is, the processor 120 may compare the first feature value with a predetermined threshold value; and in response to the first feature value exceeding the threshold value, the processor 120 may determine that a variation in the first feature value deviates from the homoeostasis maintaining region and enters the linear change region, and may determine the reference scale factor to be a scale control factor.

Further, in response to the first feature value being lower than the predetermined threshold value, the processor 120 may determine that a variation in the first feature value belongs to the homoeostasis maintaining region, and may calculate a scale control ratio to adjust a reference scale factor based on the calculated scale control ratio.

As described above, the processor 120 may determine whether the first feature value exceeds a predetermined threshold value; and in response to the first feature value exceeding the threshold value, the processor 120 may omit calculation of the scale control ratio, thereby accurately and rapidly estimating bio-information.

The processor 120 may calculate a third feature value $f_{est}$ by combining the first feature values, and may estimate bio-information based on the calculated third feature value and the determined scale factor.

For example, upon calculating the third feature value, the processor 120 may estimate bio-information using a bio-information estimation model as represented by the following Equation 5.

$$BI_{est}=SF^*(f_{est}-f_{est\_ref})+BI_{offset} \qquad [\text{Equation 5}]$$

Herein, BI denotes bio-information to be estimated, SF denotes a scale factor, $f_{est\_ref}$ denotes a reference third feature value, and $BI_{offset}$ denotes an offset value for bio-information to be estimated. $BI_{offset}$ may refer to bio-information estimated in a reference state, and may be a reference value measured by an external device for estimating bio-information, and the value may vary according to the types of bio-information to be estimated.

That is, upon calculating the third feature value, the processor 120 may estimate bio-information by multiplying a difference between the third feature value and the reference third feature value by the determined scale factor, and by adding the offset value for bio-information to the multiplied value.

In this case, the second feature value and the third feature value may be calculated by different combinations of the first feature values.

For example, the second feature value and the third feature value are calculated by a combination of the first feature values, but methods of combining the first feature values to calculate the second feature value and the third feature value may be different from each other. However, the calculation is not limited thereto, and the second feature value and the third feature value may be calculated by the same combination of the first feature values.

As described above, the bio-information estimating apparatus 100 may adaptively change the reference scale factor by using the individual scale control ratio for each of the first feature values and/or the scale control ratio calculated based on the second feature value, and thus may stably estimate bio-information.

Figure 7:
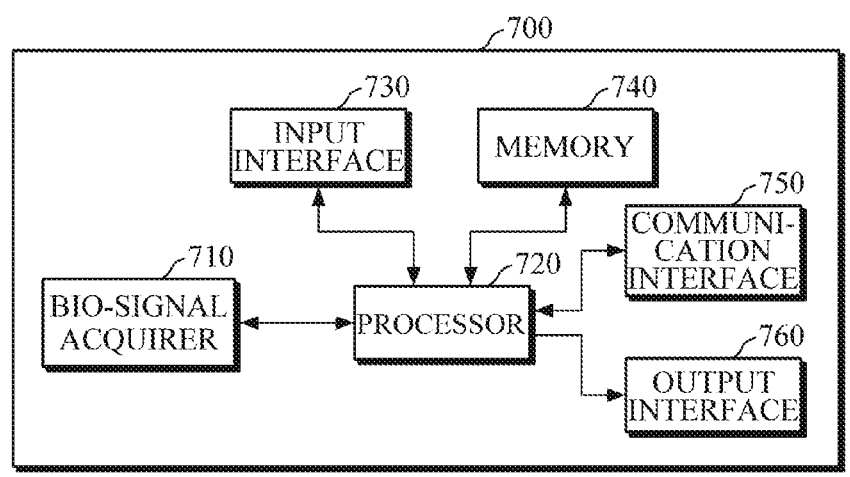
FIG. 7 is a block diagram illustrating an apparatus for estimating bio-information according to another example embodiment.

FIG. 7 is a block diagram illustrating another example of an apparatus for estimating bio-information.

Referring to FIG. 7, the bio-information estimating apparatus 700 includes a bio-signal acquirer 710, a processor 720, an input interface 730, a memory 740, a communication interface 750, and an output interface 760. Here, the bio-signal acquirer 710 and the processor 720 perform substantially the same function as the bio-signal acquirer 110 and the processor 120 described above with reference to FIG. 1, such that the following description will be made based on non-overlapping parts.

The input interface 730 may receive input of various operation signals and data required for estimating bio-information from a user.

For example, the input interface 730 may include a keypad, a dome switch, a touch pad (static pressure/capacitance), a jog wheel, a jog switch, a hardware (H/W) button, and the like. Particularly, the touch pad, which forms a layer structure with a display, may be called a touch screen.

For example, the input interface 730 may receive user feature information including one or more of age, gender, weight, body mass index (BMI), and disease history of users, or a measurement point of a bio-signal, types of a bio-signal and bio-information, and the like.

The memory 740 may store programs or commands for operation of the bio-information estimating apparatus 700, and may store data input to and output from the bio-information estimating apparatus 700. For example, the memory 740 may store the user information input through the input interface 730, the bio-signal data acquired by the bio-signal acquirer 710, the extracted first feature values, the calculated second feature value and third feature value, the scale factor, the reference scale factor, the scale control ratio, individual scale control ratios, the scale control ratio decision function, the reference first feature value, the reference second feature value, the reference third feature value, and the bio-information estimation model.

The memory 740 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the bio-information estimating apparatus 700 may operate an external storage medium, such as web storage and the like, which performs a storage function of the memory 740 on the Internet.

The communication interface 750 may perform communication with an external device. For example, the communication interface 750 may transmit, to the external device, user feature information input through the input interface 730, the bio-signal acquired by the bio-signal acquirer 710, an estimation result of bio-information of the processor 720, and the like; or may receive, from the external device, various data such as user feature information, the bio-signal, the scale control ratio decision function, the bio-information estimation model, and the like.

In this case, the external device may be medical equipment using a bio-information database (DB) and/or an estimation result of bio-information, a printer to print out results, or a display to display the estimation result of bio-information. In addition, the external device may be a digital TV, a desktop computer, a cellular phone, a smartphone, a tablet PC, a laptop computer, a personal digital assistant (PDA), a portable multimedia player (PMP), a navigation, an MP3 player, a digital camera, a wearable device, and the like, but the external device is not limited thereto.

The communication interface 750 may communicate with an external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely exemplary and is not intended to be limiting.

The output interface 760 may output at least one of a bio-signal, a feature value of a bio-signal, a multiplication coefficient ratio control factor, a multiplication coefficient ratio, and estimated bio-information.

For example, the output interface 760 may output at least one or more of the estimation result of bio-information, warning information on a state of the acquired bio-signal, and reliability of the estimated bio-information by using at least one of an acoustic method, a visual method, and a tactile method. To this end, the output interface 760 may include a display, a speaker, a vibrator, and the like.

For example, the processor 720 may measure a bio-signal in a reference state, and may output bio-signal measurement guide information for calculating the reference first feature value, the reference second feature value, the reference third feature value, and an offset value for bio-information.

In addition, the processor 720 may receive a new bio-signal from an external bio-signal database (DB) through the communication interface 750.

Figure 8:
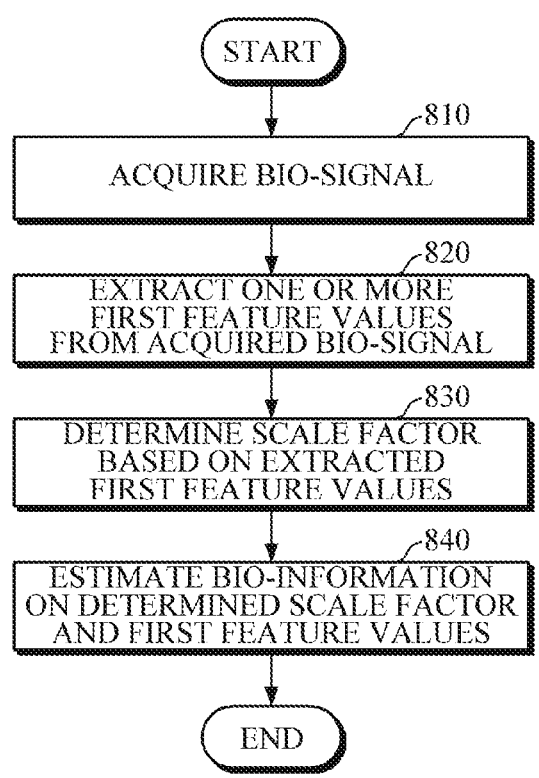
FIG. 8 is a flowchart illustrating a method of estimating bio-information according to an example embodiment.

FIG. 8 is a flowchart illustrating an example of a method of estimating bio-information. The bio-information estimating method of FIG. 8 may be performed by the bio-information estimating apparatuses 100 and 700 illustrated in FIGS. 1 and 7.

The bio-information estimating apparatus 700 may acquire a bio-signal in operation 810.

The bio-information estimating apparatus 700 may include a sensor including at least one of the following: one or more electrodes for measuring a bio-signal, a PPG sensor, an ECG sensor, a pressure sensor, and a photodetector module including a light source and a detector. The bio-information estimating apparatus 700 may directly interface with a user to acquire a bio-signal. Further, the bio-information estimating apparatus 700 is not limited thereto, and may communicate with an external device to receive bio-signal data of a user from the external device.

Upon acquiring the bio-signal, the bio-information estimating apparatus 700 may extract one or more first feature values $f_1$ from the acquired bio-signal in operation 820.

The first feature values, which are extracted from the bio-signal, may indicate features having a predetermined correlation with bio-information desired to be estimated, and may vary depending on the types of bio-information.

Upon extracting the first feature values from the bio-signal, the bio-information estimating apparatus 700 may convert the first feature values. For example, the bio-information estimating apparatus 700 may normalize the first feature values by dividing the extracted first feature value by a reference first feature value extracted in a reference state.

In this case, the reference state is a resting state except for a sleep state, and may refer to, for example, a state in which pulse and respiration rates are stable, or a state in which blood pressure measured by an external device for measuring blood pressure is maintained without substantial change. The reference state may be measured from a test subject while the test subject is awake and resting without exercising.

Further, a reference second feature value and a reference third value, which will be described later, may refer to a second feature value and a third feature value which are calculated based on the reference first feature value extracted in the reference state.

Then, the bio-information estimating apparatus 700 may determine a scale factor based on the extracted first feature values in operation 830. Operation 830 may include a first step of calculating a scale control factor, and a second step of multiplying a default scale factor by the scale control ratio. For example, the bio-information estimating apparatus 700 may store the default scale factor in a memory, and may adjust the default scale factor by multiplying the default scale factor and the scale control ratio. The term "default scale factor" may be also referred to as "reference scale factor."

Specifically, the bio-information estimating apparatus 700 may calculate a second feature value $f_f$ by combining the first feature values, and may calculate a scale control ratio based on the second feature value.

For example, upon calculating one or more first feature values, the bio-information estimating apparatus 700 may calculate the second feature value by using an individual variation and/or a combined variation of the first feature values.

In this case, the combined variation may refer to a difference between a value, obtained by linear combination of the first feature values $f_{1a}$ and $f_{1b}$ (e.g., addition, subtraction, and multiplication of $f_{1a}$ and $f_{1b}$, a combination thereof, etc.), and the reference second feature value $f_{sc,\ ref}$; and the individual variation may refer to a difference between each of the first feature values $f_{1a}$ and $f_{1b}$ and the reference second feature value $f_{sc,\ ref}$.

The bio-information estimating apparatus 700 may apply a weight to a first feature value, having a higher correlation with bio-information to be estimated than other first feature values among the extracted first feature values.

As described above, upon calculating the second feature value, the bio-information estimating apparatus 700 may calculate a scale control ratio based on the second feature value, and may determine a scale factor by adjusting a reference scale factor based on the calculated scale control ratio.

For example, the bio-information estimating apparatus 700 may calculate a scale control ratio according to a magnitude of the second feature value by applying the calculated second feature value to a scale control ratio decision function.

Here, a scale control ratio decision function may have a valley shape, in which the scale control ratio has a minimum value $\rho_{min}$ at a point of the reference second feature value $f_{sc\_ref}$, and increases with the change in the second feature value from the reference second feature value, and in the case where the second feature value falls outside a threshold range, the scale control ratio is saturated to a predetermined scale control ratio Here, the threshold range may indicate an interval between a low point $\mu_{low}$ and a high point $\mu_{high}$ of the second feature value. In other words, the threshold range may indicate a region where the first feature value is changed from the homoeostasis maintaining region, and a region where the scale control ratio changes adaptively. That is, in the case where the second feature value $f_{sc}$ changes within the predetermined threshold range, the scale control ratio increases in both directions from the reference second feature value.

As described above, since the scale control ratio has a minimum value at a point of the reference second feature value, the change of bio-signal features in a stable state, such as a reference state, may have a small effect on estimation of bio-information; and as the second feature value deviates from the reference state, the scale control ratio for estimating bio-information increases. Accordingly, as an amplitude of a bio-signal increases, the change of the bio-signal features may have a greater effect on estimation of bio-information.

Then, as the second feature value continuously changes to fall outside the threshold range, the scale control ratio is saturated to a predetermined scale control ratio (e.g., 1), such that the bio-information estimating apparatus 700 may determine the predetermined reference scale factor itself to be a scale factor.

In another example, the bio-information estimating apparatus 700 may calculate an individual scale control ratio for each of the first feature values based on the scale control ratio decision function for each of the first feature values.

For example, upon extracting first feature values $f_{1a}$, $f_{1b}$, and $f_{1c}$, instead of generating a second feature value by combining the first feature values, the bio-information estimating apparatus 700 may calculate individual scale control ratios $\rho_1$, $\rho_2$, and $\rho_3$ using scale control ratio functions $\rho_1(f_{1a})$, $\rho_2(f_{1b})$, and $\rho_3(f_{1c})$ for each of the first feature values, and may use a statistical value of the individual scale control ratios as a scale control ratio.

As described above, upon calculating the scale control ratio, the bio-information estimating apparatus 700 may determine a scale factor by adjusting a reference scale factor using the calculated scale control ratio.

Then, upon determining the scale factor, the bio-information estimating apparatus 700 may estimate bio-information based on the determined scale factor and the first feature values in operation 840. Operation 840 may include a first step of subtracting a reference feature $f_{est\_ref}$ from an extracted feature $f_{est}$ of the bio-signal to obtain a first value, a second step of multiplying the first value by the adjusted scale factor SF to obtain a second value, and a third step of adding an offset value $BI_{offset}$ to the second value to obtain an estimated result $BI_{est}$.

For example, the bio-information estimating apparatus 700 may calculate a third feature value $f_{est}$ by combining the first feature values, and may estimate bio-information based on the calculated third feature value and the determined scale factor.

Upon calculating the third feature value, the bio-information estimating apparatus 700 may estimate bio-information by multiplying a difference between the third feature value and the reference third feature value by the determined scale factor, and by adding the offset value for bio-information to the multiplied value.

Figure 9:
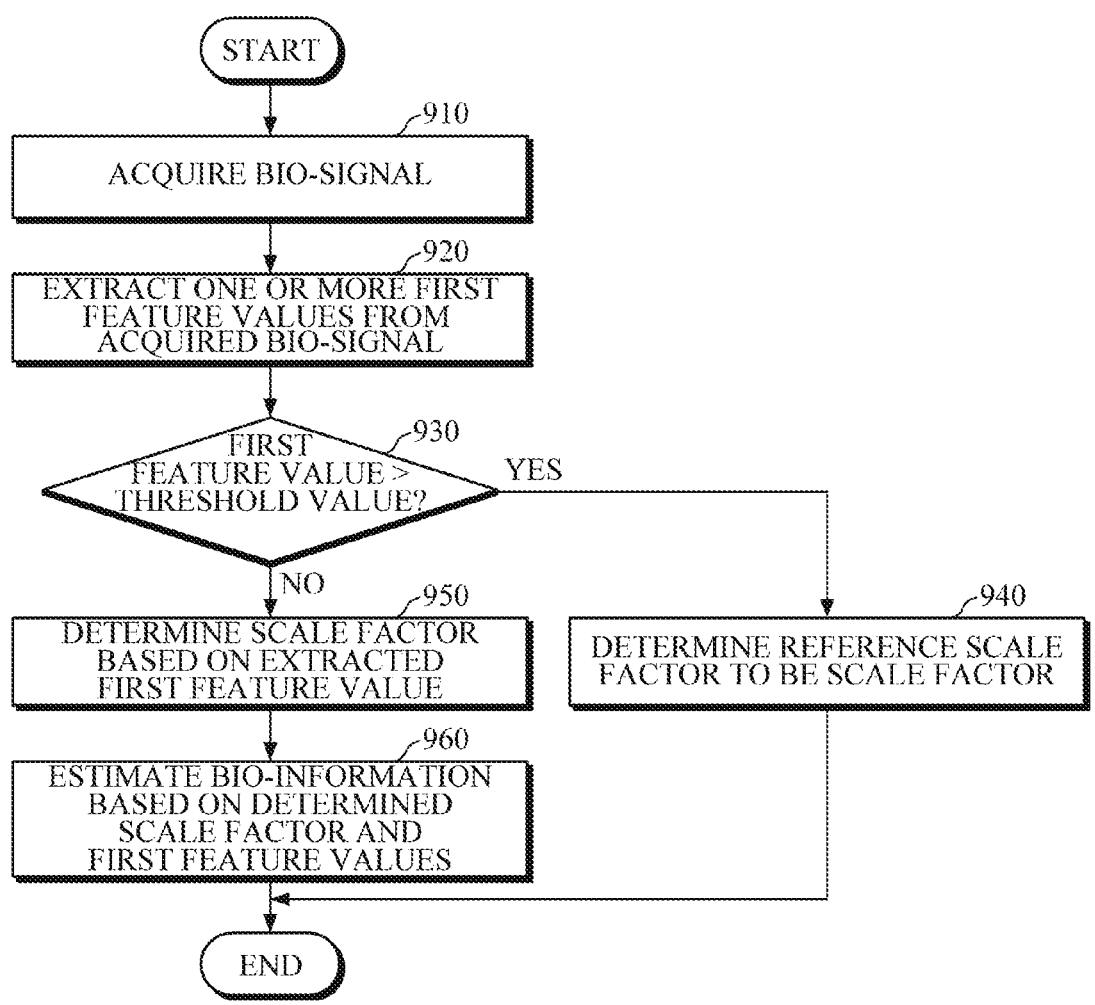
FIG. 9 is a flowchart illustrating a method of estimating bio-information according to another example embodiment.

FIG. 9 is a flowchart illustrating another example of a method of estimating bio-information.

Acquiring of a bio-signal in operation 910, extracting one or more first feature values from the acquired bio-signal in operation 920, determining a scale factor based on the extracted first feature values in operation 950, and estimating bio-information based on the determined scale factor and the first feature values in operation 960 are substantially the same as the acquiring of the bio-signal in operation 810, the extracting of the one or more first feature values from the acquired bio-signal in operation 820, the determining of the scale factor based on the extracted first feature values in operation 830, and the estimating of the bio-information based on the determined scale factor and the first feature values in operation 840, such that the following description will be made based on non-overlapping parts.

The bio-information estimating apparatus 700 may acquire a bio-signal in operation 910.

Upon acquiring the bio-signal, the bio-information estimating apparatus 700 may extract one or more first feature values from the acquired bio-signal in operation 920.

Then, the bio-information estimating apparatus 700 may determine whether the first feature value exceeds a predetermined threshold value in operation 930.

For example, the bio-information estimating apparatus 700 may compare the extracted first feature value with a value at a predetermined low point $\mu_{low}$ or a predetermined high point $\rho_{high}$ of the scale control ratio decision function, and may determine whether the first feature value is lower than the predetermined low point $\mu_{low}$ or higher than the predetermined high point $\mu_{high}$.

Upon determining that the first feature value exceeds the threshold value, the bio-information estimating apparatus 700 may determine the reference scale factor to be a scale factor in operation 940.

For example, the bio-information estimating apparatus 700 may compare the first feature value with a predetermined threshold value; and in response to the first feature value exceeding the threshold value based on the comparison, the bio-information estimating apparatus 700 may determine that a variation in the first feature value deviates from the homoeostasis maintaining region and enters the linear change region, and may determine the reference scale factor to be a scale control factor.

As described above, the bio-information estimating apparatus 700 may determine whether the first feature value exceeds a predetermined threshold value; and in response to the first feature value exceeding the threshold value, the bio-information estimating apparatus 700 may omit calculation of the scale control ratio, thereby accurately and rapidly estimating bio-information.

Further, in response to the first feature value being lower than the predetermined threshold value, the bio-information estimating apparatus 700 may determine that a variation of the bio-signal belongs to the homoeostasis maintaining region, and may determine a scale factor based on the extracted first feature value in operation 950.

Upon determining the scale factor, the bio-information estimating apparatus 700 may estimate bio-information based on the determined scale factor and the first feature values in operation 960.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing example embodiments are merely example and are not to be construed as limiting. The present teaching can be readily applied to other types of apparatuses. Also, the description of the example embodiments is intended to be illustrative, and not to limit the scope of the claims, and many alternatives, modifications, and variations will be apparent to those skilled in the art.

What is claimed is:

1. An apparatus for estimating bio-information, the apparatus comprising:
a photoplethysmography (PPG) sensor configured to acquire a PPG signal; and
a processor configured to:
extract, from the PPG signal, first feature values comprising a cardiac output (CO) feature value and a total peripheral resistance (TPR) feature value,
obtain a second feature value based on a combined variation of the CO feature value and the TPR feature value;
obtain a scale control ratio based on a determination of whether the second feature value belongs to a homoeostasis maintaining region in which a variation in the second feature value is smaller than a variation in the PPG signal, a linear change region in which a correlation between the variation in the second feature value and the variation in the PPG signal is greater than or equal to a predetermined correlation value, or a non-linear saturation region in which the correlation between the variation in the second feature value and the variation in the PPG signal is less than the predetermined correlation value;
adaptively determine a scale factor based on the scale control ratio that changes according to a relation between the variation in the second feature value and the variation in the PPG signal; and
estimate the bio-information based on the scale factor and the first feature values.

2. The apparatus of claim 1, wherein the processor is further configured to calculate the second feature value by combining an individual variation of the CO feature value and the TPR feature value, with the combined variation of the CO feature value and the TPR feature value.

3. The apparatus of claim 1, wherein the processor is further configured to calculate the scale control ratio according to a magnitude of the second feature value by applying the second feature value to a scale control ratio decision function.

4. The apparatus of claim 3, wherein the scale control ratio decision function is expressed as a graph having a valley shape, in which the scale control ratio has a minimum value at a point of a reference second feature value and increases with a change in the second feature value from the reference second feature value, and the scale control ratio is saturated to a predetermined scale control ratio in an area of the graph where the second feature value falls outside a threshold range.

5. The apparatus of claim 1, wherein the processor is further configured to calculate a third feature value by combining the first feature values, and estimate the bio-information based on the third feature value and the scale factor.

6. The apparatus of claim 5, wherein the processor is further configured to estimate the bio-information by multiplying a difference between the third feature value and a reference third feature value by the scale factor, and adding an offset value to the multiplied difference.

7. The apparatus of claim 1, wherein in response to the first feature values exceeding a predetermined threshold value, the processor is further configured to determine a reference scale factor to be the scale factor.

8. The apparatus of claim 1, wherein the processor is further configured to normalize the first feature values based on a reference first feature value.

9. The apparatus of claim 1, wherein the bio-information comprises at least one of blood pressure, cardiac output, blood glucose, triglycerides, and keratin.

10. A method of estimating bio-information, the method comprising:
acquiring a photoplethysmography (PPG) signal;
extracting, from the PPG signal, first feature values comprising a cardiac output (CO) feature value and a total peripheral resistance (TPR) feature value;
obtaining a second feature value based on a combined variation of the CO feature value and the TPR feature value;
obtaining a scale control ratio based on a determination of whether the second feature value belongs to a homoeostasis maintaining region in which a variation in the second feature value is smaller than a variation in the PPG signal, a linear change region in which a correlation between the variation in the second feature value and the variation in the PPG signal is greater than or equal to a predetermined correlation value, or a non-linear saturation region in which the correlation between the variation in the second feature value and the variation in the PPG signal is less than the predetermined correlation value;
adaptively determining a scale factor based on the scale control ratio that changes according to a relation between the variation in the second feature value and the variation in the PPG signal; and estimating the bio-information based on the scale factor and the first feature values.

11. The method of claim 10, wherein the obtaining the second feature value comprises obtaining the second feature value further based on an individual variation of the CO feature value and the TPR feature value.

12. The method of claim 10, wherein the obtaining the scale control ratio comprises calculating the scale control ratio according to a magnitude of the second feature value by applying the second feature value to a scale control ratio decision function.

13. The method of claim 12, wherein the scale control ratio decision function is expressed as a graph having a valley shape, in which the scale control ratio has a minimum value at a point of a reference second feature value and increases with a change in the second feature value from the reference second feature value, and the scale control ratio is saturated to a predetermined scale control ratio in an area of the graph where the second feature value falls outside a threshold range.

14. The method of claim 10, wherein the estimating the bio-information comprises:

calculating a third feature value by combining the first feature values;

multiplying a difference between the third feature value and a reference third feature value by the scale factor; and adding an offset value to the multiplied difference to estimate the bio-information.

15. The method of claim 10, wherein the obtaining the scale factor comprises:

determining whether the first feature values exceed a predetermined threshold value; and upon determining that the first feature values exceed the predetermined threshold value, determining a reference scale factor to be the scale factor.

* * * * *